(12) United States Patent
Ohno et al.

(10) Patent No.: US 7,812,202 B2
(45) Date of Patent: Oct. 12, 2010

(54) PROCESS FOR PRODUCING HEXAFLUORO-1,3-BUTADIENE

(75) Inventors: Hiromoto Ohno, Kawasaki (JP); Toshio Ohi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/298,863

(22) PCT Filed: Apr. 25, 2007

(86) PCT No.: PCT/JP2007/058980
§ 371 (c)(1),
(2), (4) Date: Jan. 27, 2009

(87) PCT Pub. No.: WO2007/125972
PCT Pub. Date: Aug. 11, 2007

(65) Prior Publication Data
US 2009/0216053 A1    Aug. 27, 2009

(30) Foreign Application Priority Data
Apr. 28, 2006 (JP) ............................. 2006-126977

(51) Int. Cl.
C07C 17/00 (2006.01)
(52) U.S. Cl. ...................................................... 570/156
(58) Field of Classification Search .................. 570/156
See application file for complete search history.

(56) References Cited
FOREIGN PATENT DOCUMENTS
WO    2005/023734 A1    3/2005
WO    2006/077727 A1    7/2006

OTHER PUBLICATIONS

Makhmutov et al (RU 2247104, Chemical abstract), 2005.*
James L. Adcock, et al., "Aerosol Direct Fluorination of C1 and C2 Chlorocarbons," Ind. Eng. Chem. Res., 1989, pp. 1547-1549, vol. 28, No. 10.
N.M. Karimova, et al., "Synthesis of 1,2,3,4-tetrachlorohexafluorobutane," Russian Chemical Bulletin, International Edition, Oct. 2004, pp. 2336-2337, vol. 53, No. 10.

* cited by examiner

*Primary Examiner*—Jafar Parsa
(74) *Attorney, Agent, or Firm*—Sughrue Mion, PLLC

(57) ABSTRACT

Disclosed is a process for producing hexafluoro-1,3-butadiene, which is used for an etching gas capable of being used in fine processing for semiconductors, safely in industrialization and at low cost economically. Specifically disclosed is a process for producing hexafluoro-1,3-butadiene comprises (1) a step comprising allowing a compound having four carbon atoms each which bonds to an atom selected from the group consisting of a bromine atom, an iodine atom and a chlorine atom, to react with a fluorine gas in the presence of a diluting gas in a gas phase, thereby preparing a mixture containing a product (A), and (2) a step comprising eliminating halogens excluding a fluorine atom with a metal from the product (A) prepared in the step (1) in the presence of a solvent, thereby preparing a mixture containing hexafluoro-1,3-butadiene.

19 Claims, No Drawings

PROCESS FOR PRODUCING HEXAFLUORO-1,3-BUTADIENE

CROSS REFERENCE TO RELATED APPLICATIONS

This application is a National Stage of International Application No. PCT/JP2007/058980 filed Apr. 25, 2007, claiming priority based on Japanese Patent Application No. 2006-126977 filed Apr. 28, 2006, the contents of all of which are incorporated herein by reference in their entirety.

TECHNICAL FIELD OF THE INVENTION

The present invention relates to a process for producing hexafluoro-1,3-butadiene. Specifically, it relates to a process for producing hexafluoro-1,3-butadiene which is useful as an etching gas for semiconductors.

BACKGROUND OF THE INVENTION

Hexafluoro-1,3-butadiene (referred to "C4F6" or "HFBD" in this specification) is noted as, for example, an etching gas for semiconductor fine processing.

The following methods are conventionally known as a process for producing hexafluoro-1,3-butadiene.

(1) Patent document 1 discloses a process for producing perfluorinated olefins by allowing a perfluorinated alkyl halide to react with a Grignard reagent at a temperature of about from $-60°$ C. to $200°$ C.

(2) Patent document 2 discloses a process for producing hexafluoro-1,3-butadiene by eliminating iodine fluoride from $ICF_2CF_2CF_2CF_2I$ by the use of a Mg, Zn, Cd or Li organic metal compound in the presence of a hydrocarbon non-proton solvent or in the presence of a non-proton polar solvent such as ether or cyclic ethers at a temperature of from $-80$ to $150°$ C.

(3) Patent document 3 discloses a process for producing hexafluoro-1,3-butadiene by eliminating iodine fluoride from $BrCF_2CF_2CF_2CF_2I$ or $BrCF_2CF_2CF_2CF_2Br$ by the use of a Mg or Li organometallic compound in the presence of a hydrocarbon neutral solvent or in an ether, cyclic ether or a mixture thereof neutral solvent at a temperature of from $-80$ to $150°$ C.

(4) Patent document 4 discloses a process for producing hexafluoro-1,3-butadiene by eliminating iodine fluoride from $ICF_2CF_2CF_2CF_2I$ in the presence of metal zinc, and at least one nitrogen containing compound selected from N,N-dimethyl formamide and N-methyl-2-pyrrolidone.

(5) Patent document 5 discloses a process for producing hexafluoro-1,3-butadiene by using, as a raw material, $ICF_2CF_2CF_2CF_2I$ or $BrCF_2CF_2CF_2CF_2Br$ in an organic solvent in the presence of at least one metal selected from Mg, Zn, Cd, Al, Cu, Na and Li, and RX (X=Cl, Br or I) and/or $I_2$. In this process, RX is added in an amount of 0.05 to 0.5 equivalent based on the $\alpha,\omega$-dihalogenated perfluoroalkane.

(6) Patent document 6 discloses a process for producing hexafluoro-1,3-butadiene by heating or boiling refluxing $XCF_2CFXCFYCF_2X$ (X=Cl, Br or I, Y=Cl, Br, I or F) together with at least one metal selected from Mg, Zn, Cd, Al, Cu, Na and Li, and halogenated alkyl RX (X=Cl, Br or I) in an organic solvent. In this process, RX, which is a catalyst, is added in an amount of 0.05 to 0.5 equivalent based on tetrahalogenated perfluorobutane.

Patent Document 1: JP-B-S49 (1974)-39648

Patent Document 2: JP-A-S62 (1987)-26340

Patent Document 3: U.S. Pat. No. 2,589,108

Patent Document 4: JP-A-2001-192345

Patent Document 5: JP-A-2001-192346

Patent Document 6: JP-A-2001-192347

DISCLOSURE OF THE INVENTION

Object of the Invention

The above processes, however, have the following problems. In the processes (1) to (5), when an organic metal compound is used industrially, the preparation of the organic metal compound has a danger problem. For example, the synthesis of the Grignard reagent has danger. Moreover, since halogens, which are used as a raw material, such as iodine or bromine are expensive, the processes have a problem in industrialization. The process (6) also has a problem in industrialization because a bromine compound needs to be added as a catalyst.

Under the circumstances, it is an object of the invention to provide a process for producing a HFBD, which is used for an etching gas capable of being used in fine processing for semiconductors, safely in industrialization and at low cost economically.

Means for Solving the Object

The present inventors have been studied in order to solve the object and found that hexafluoro-1,3-butadiene can be produced in good yield industrially and at low cost economically by the following steps. The steps comprise preparing a mixture containing a product (A) by allowing a compound having four carbon atoms each which bonds to an atom selected from the group consisting of a bromine atom, an iodine atom and a chlorine atom to react with a fluorine gas in a gas phase, and preparing a mixture containing hexafluoro-1,3-butadiene by eliminating halogens excluding a fluorine atom with a metal from the product (A) in the presence of a solvent. Thus, the present invention has been accomplished.

EFFECT OF THE INVENTION

The present invention can provide a process for producing a HFBD, which has safety in industrialization and is advantageous economically, by a step of allowing a compound having four carbon atoms each which bonds to an atom selected from the group consisting of a bromine atom, an iodine atom and a chlorine atom, to react with a fluorine gas in a gas phase, thereby preparing a mixture containing a product (A), and a step of eliminating halogens excluding a fluorine atom with a metal from the product (A) in the presence of a solvent, thereby preparing a mixture containing hexafluoro-1,3-butadiene.

BEST EMBODIMENT FOR CARRYING OUT THE INVENTION

The preferred embodiments of the present invention will be described in detail, but the present invention is not limited by these embodiments. In the present invention, various modifications can be made within the concept and achievement of the present invention.

The production process of the present invention comprises the step (1) of allowing a compound having four carbon atoms each which bonds to an atom selected from the group consisting of a bromine atom, an iodine atom and a chlorine atom, to react with a fluorine gas in the presence of a diluting gas in a gas phase, thereby preparing a mixture containing a product (A), and the step (2) of eliminating halogens excluding a fluorine atom with a metal from the product (A) prepared in the step (1) in the presence of a solvent, thereby preparing a mixture containing hexafluoro-1,3-butadiene.

In the step (1) (direct fluorinating step), the reaction of allowing a compound having four carbon atoms each which bonds to an atom selected from the group consisting of a bromine atom, an iodine atom and a chlorine atom, to react with a fluorine gas in the presence of a diluting gas in a gas phase is preferably carried out in the absence of a catalyst. The diluting gas is preferably at least one gas selected from the group consisting of nitrogen, helium, argon, neon and hydrogen fluoride. In the present specification, nitrogen, helium, argon and neon are inclusively referred to inert gases.

The compound having four carbon atoms contains an atom selected from the group consisting of a bromine atom, an iodine atom and a chlorine atom, for each carbon atom and preferably one chlorine for each carbon atom. That is to say, in the compound having four carbon atoms, the atom selected from the group consisting of a bromine atom, an iodine atom and a chlorine atom, preferably a chlorine atom is bonded to each carbon one by one. The compound containing a bromine atom or an iodine atom is expensive and a substance having high corrosion properties. Therefore, it occasionally brings an increase in cost. An example of the compound having four carbon atoms may include 1,2,3,4-tetrachlorobutane. The 1,2,3,4-tetrachlorobutane is produced, as a by product, in a step of industrially producing a chloroprene rubber by using 1,3-butadiene as a raw material as indicated in the following formulas that the formula (1) indicates an objective reaction and the formula (2) indicates a byproduct reaction, and it is made harmless by burning treatment or the like together with other chlorine compound byproducts in the present condition.

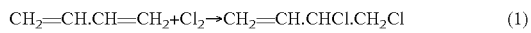
$$CH_2=CH.CH=CH_2+Cl_2 \rightarrow CH_2=CH.CHCl.CH_2Cl \qquad (1)$$

$$CH_2=CH.CH=CH_2+ 2Cl_2 \rightarrow CH_2Cl.CHCl.CHCl.CH_2Cl \qquad (2)$$

Accordingly, 1,2,3,4-tetrachlorobutane, which is the byproduct, is preferably used as a raw material from the economical viewpoint. That is to say, the production process of the present invention further comprises a step (3) of halogenating (brominating, iodizing or chlorinating) 1,3-butadiene thereby preparing the compound having four carbon atoms. The step (1) preferably comprises allowing the compound having four carbon atoms prepared in the step (3) to react with a fluorine gas, thereby preparing the mixture containing the product (A).

Furthermore, the production process of the present invention preferably comprises the step (1) of allowing 1,2,3,4-tetrachlorobutane to react with a fluorine gas in the presence of a diluting gas in a gas phase thereby preparing a mixture containing 1,2,3,4-tetrachlorohexafluorobutane and the step (2) of dechlorinating 1,2,3,4-tetrachlorohexafluorobutane prepared in the step (1) by a metal in the presence of a solvent thereby preparing a mixture containing hexafluoro-1,3-butadiene. This case will be described hereinafter.

In the step (1), the reaction is preferably carried out in the absence of a catalyst. The mixture containing 1,2,3,4-tetrachlorohexafluorobutane contains the resulting 1,2,3,4-tetrachlorohexafluorobutane, the resulting hydrogen fluoride, unreacted 1,2,3,4-tetrachlorobutane, an intermediate of the reaction in the step (1) such as 1,2,3,4-tetrachlorotetrafluorobutane or 1,2,3,4-tetrachloropentafluorobutane, and a diluting gas.

In this case, the reaction in the step (1) is represented by the following formula (3).

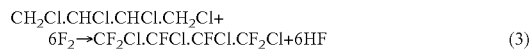
$$CH_2Cl.CHCl.CHCl.CH_2Cl+ 6F_2 \rightarrow CF_2Cl.CFCl.CFCl.CF_2Cl+6HF \qquad (3)$$

In this step, since a fluorine gas having very high reactivity is used, the reaction of an organic compound, which is a substrate, with a fluorine gas occasionally causes explosion or corrosion. Furthermore, the reaction occasionally causes cut of carbon bonding or polymerization due to exothermic reaction, or side reactions such as rapid reaction or explosion due to carbon generation or deposition. The substitution of one C—H bond with C—F bond generates a heat of reaction of about −110 kcal/mol. For example, the direct fluorinating step of allowing 1,2,3,4-tetrachlorobutane to react with a fluorine gas generates a heat of reaction of about −660 kcal/mol. The heat of reaction is in proportion to the mole number of a fluorine gas, namely, the heat of reaction is larger in proportion with the increase of the fluorine gas amount. Therefore, the step easily causes cut of carbon bonding or explosion, and further causes a decline in the yield and thereby sometimes causes a problem in industrial production or operation.

On this account, in order to depress rapid generation of a heat of reaction in the direct fluorinating step, it is preferred to employ, for example, a method of diluting a fluorine gas with the above inert gas such as nitrogen or helium and a method of diluting the organic compound, which is a substrate, also with the above inert gas or hydrogen fluoride. It is preferred to, further, employ a method of carrying out the reaction in a low temperature region and a method of carrying out the reaction in a gas phase by dividedly feeding a fluorine gas so as to contact the fluorine gas in limited amounts with the organic compound, which is a substrate.

In the step (1), into a reactor (A) equipped with at least two feed openings, a mixed gas (A) of 1,2,3,4-tetrachlorobutane and the diluting gas is fed from at least one feed opening and a mixed gas (B) of a fluorine gas and the diluting gas is fed from at least one of the other feed openings and thereby 1,2,3,4-tetrachlorobutane is allowed to react with a fluorine gas in the reactor (A), to prepare a mixture containing 1,2,3,4-tetrachlorohexafluorobutane. The concentration of 1,2,3,4-tetrachlorobutane is preferably 0.5 to 4 mol % based on the total amount of the mixed gases (A) and (B). When the organic compound, which is a substrate, is exposed to fluorine in a 1,2,3,4-tetrachlorobutane concentration of more than 4 mol %, burning or explosion will be occasionally taken place. The step (1), further, is a process of preparing a mixture containing 1,2,3,4-tetrachlorohexafluorobutane by, into a reactor (A) having at least two feed openings, feeding a mixed gas (A) of 1,2,3,4-tetrachlorobutane and the diluting gas from at least one feed opening and feeding a mixed gas (B) of a fluorine gas and the diluting gas from at least one of the other feed openings, thereby allowing 1,2,3,4-tetrachlorobutane to react with a fluorine gas in the reactor (A). The fluorine gas concentration is preferably 0.5 to 10 mol %, more preferably 0.5 to 6 mol % based on the total amount of the mixed gases (A) and (B). The diluting gas is preferably fed in a concentration of 86 to 99 mol % based on the total amount of the gases fed to the reactor, namely the total amount of the gases (A) and (B).

The step (1) is preferably a process of preparing a mixture containing 1,2,3,4-tetrachlorohexafluorobutane by, into a reactor (A) having at least three feed openings, feeding a mixed gas (A) of 1,2,3,4-tetrachlorobutane and the diluting gas from at least one feed opening and feeding a mixed gas (B) of a fluorine gas and the diluting gas from at least two feed openings of the other feed openings, thereby allowing 1,2,3, 4-tetrachlorobutane to react with a fluorine gas in the reactor. Furthermore, from the viewpoint of preventing the occurrence of burning or explosion, the step (1) is preferably a process of preparing a mixture containing 1,2,3,4-tetrachlorohexafluorobutane by, into a reactor having at least three feed openings, feeding a mixed gas (A) of 1,2,3,4-tetrachlorobutane and the diluting gas from at least two feed openings and feeding a mixed gas (B) of a fluorine gas and the diluting gas from at least one of the other feed openings, thereby allowing 1,2,3,4-tetrachlorobutane to react with a fluorine gas in the reactor.

The step (1) is preferably a process of preparing a mixture containing 1,2,3,4-tetrachlorohexafluorobutane by allowing 1,2,3,4-tetrachlorobutane to react with a fluorine gas at a pressure of from 0.05 to 1 MPa. Since the range where explosion will be occurred is generally wider in proportion with the pressure increase, the reaction is preferably carried put at a low pressure. In the step (1), the reaction of 1,2,3,4-tetrachlorobutane with a fluorine gas is carried out at a temperature of preferably from 50 to 500° C., more preferably 150 to 450° C. thereby preparing a mixture containing 1,2,3,4-tetrachlorohexafluorobutane.

The material of the reactor is preferably a material having resistance to a corrosive gas, for example, an alloy containing nickel as an essential component, such as nickel, Inconel or Hastelloy.

After the step (1), at least one part of the mixture containing 1,2,3,4-tetrachlorohexafluorobutane may be taken out and liquid-liquid separated by, for example, cooling. That is to say, it may be separated into a hydrogen fluoride-rich phase and a 1,2,3,4-tetrachlorohexafluorobutane-rich phase. The hydrogen fluoride-rich phase contains hydrogen fluoride and further contains small amounts of organic substances such as an intermediate of the step (1), 1,2,3,4-tetrachlorohexafluorobutane and the like. The 1,2,3,4-tetrachlorohexafluorobutane-rich phase contains 1,2,3,4-tetrachlorohexafluorobutane and further contains hydrogen fluoride and a small amount of an intermediate of the step (1). The diluting gases (inert gases) other than hydrogen fluoride are removed by the liquid-liquid separation process. The hydrogen fluoride-rich phase, further, may be circulated as a diluting gas in the direct fluorinating process.

The production process of the present invention preferably comprises, further, a step (4) of allowing the resulting 1,2,3,4-tetrachlorohexafluorobutane-rich phase prepared by liquid-liquid separation of the mixture containing 1,2,3,4-tetrachlorohexafluorobutane to contact with an alkali, thereby preparing a crude 1,2,3,4-tetrachlorohexafluorobutane. In the step (4) (alkali contact process 1), the hydrogen fluoride contained in the 1,2,3,4-tetrachlorohexafluorobutane-rich phase is washed with, for example, an alkali aqueous solution.

Examples of the alkali aqueous solution may include sodium hydroxide aqueous solution, potassium hydroxide aqueous solution or the like. Moreover, the phase may be contacted with a purifying agent obtainable from an alkali metal compound, an alkaline earth metal compound, a carbonaceous solid material, alumina or zeolite. The hydrogen fluoride may be recovered in an aqueous state. The alkali contact process is preferably carried out at a temperature of from −10 to 70° C.

The production process of the present invention preferably comprises, further, a step (5) of dehydrating the crude 1,2,3,4-tetrachlorohexafluorobutane prepared in the step (4) thereby preparing a crude 1,2,3,4-tetrachlorohexafluorobutane.

For the dehydration, it is preferred to use zeolite, for example, molecular sieves 3A, 4A or 5A. The dehydration process is preferably carried out at a temperature of from −10 to 70° C.

It is particularly preferred to successively carry out the dehydration of the crude 1,2,3,4-tetrachlorohexafluorobutane in the step (5) (dehydration step) because the resulting crude 1,2,3,4-tetrachlorohexafluorobutane prepared through the alkali contact process contains moisture. That is to say, the production process of the present invention preferably comprises the step (4) of allowing the resulting 1,2,3,4-tetrachlorohexafluorobutane-rich phase prepared by liquid-liquid separating the mixture containing 1,2,3,4-tetrachlorohexafluorobutane prepared in the step (1), to contact with an alkali, thereby preparing a crude 1,2,3,4-tetrachlorohexafluorobutane, a step (5) of dehydrating the crude 1,2,3,4-tetrachlorohexafluorobutane prepared in the step (4), thereby preparing a crude dehydrated 1,2,3,4-tetrachlorohexafluorobutane, and the step (2) of dechlorinating the crude dehydrated 1,2,3,4-tetrachlorohexafluorobutane prepared in the step (5), by a metal, thereby preparing a mixture containing hexafluoro-1,3-butadiene.

At least one part of the crude dehydrated 1,2,3,4-tetrachlorohexafluorobutane prepared by the step (5) may be introduced into at least one distillation column by means of a pump or a compressor. In the distillation column, it is separated into the intermediate or the like and an objective 1,2,3,4-tetrachlorohexafluorobutane. At least one part of the intermediate may be circulated in the step (1). The production process of the present invention preferably comprises, further, a step (6) of feeding at least one part of the crude 1,2,3,4-tetrachlorohexafluorobutane prepared by the step (5) into at least one distillation column, separating the intermediate prepared in the step (1) and feeding at least one part of the unreacted materials to the reactor (A). In the step (6), the intermediate and low boiling components such as nitrogen, oxygen, carbon monoxide or carbon dioxide are removed from the crude 1,2,3,4-tetrachlorohexafluorobutane prepared in the step (5).

The step (2) is a process of dechlorinating the 1,2,3,4-tetrachlorohexafluorobutane prepared in the step (1) by a metal in the presence of a solvent, thereby preparing a mixture containing hexafluoro-1,3-butadiene.

In the step (2), it is preferred to use the 1,2,3,4-hexafluorobutane (purified product) obtainable by separating the intermediate as described above. Specifically, such 1,2,3,4-hexafluorobutane is introduced first into an SUS reactor equipped with a stirrer and a jacket by means of a pump, and a solvent is added to it. The weight ratio of the 1,2,3,4-hexafluorobutane to the solvent (the 1,2,3,4-hexafluorobutane/the solvent) is preferably from 0.4 to 1.8.

Next, while the solution in the above weight ratio thus prepared is stirred also with keeping at a temperature of usually from 20 to 150° C., preferably 30 to 95° and at a pressure of usually from 0.05 to 1 MPa, a granulated or powdery metal is fed in limited amounts to the solution. The weight ratio of 1,2,3,4-tetrachlorohexafluorobutane to the metal is preferably from 1 to 12.

The solvent is preferably an organic solvent and/or water. The organic solvent and water can be used in an arbitrary ratio, and further water may be used singly.

The organic solvent is an alcohol. The alcohol is preferably at least one selected from the group consisting of methanol, ethanol, isopropyl alcohol and octanol.

The metal is preferably at least one selected from the group consisting of Mg, Zn, Al, Cu, Na and Li.

Furthermore, at least one part of the mixture containing hexafluoro-1,3-butadiene prepared in the step (2) may be introduced into the distillation column and separated into a phase containing the solvent essentially and a phase containing hexafluoro-1,3-butadiene.

The production process of the present invention, moreover, comprises a step (7) of preparing a crude hexafluoro-1,3-butadiene by allowing the mixture containing hexafluoro-1,3-butadiene prepared in the step (2), to contact with an alkali in order to remove hydrogen fluoride contained in the mixture containing hexafluoro-1,3-butadiene (alkali contact process 2). In the step, it is preferred to allow the phase containing hexafluoro-1,3-butadiene essentially to contact with the alkali after introducing the mixture into the distillation column.

Examples of the alkali aqueous solution may include a sodium hydroxide aqueous solution and a potassium hydroxide aqueous solution. The phase may be contacted with a purifying agent obtainable from an alkali metal compound, an alkaline earth metal compound, a carbonaceous solid material, alumina or zeolite, or soda lime used generally. The alkali contact process is preferably carried out at a temperature of from −15 to 60° C.

The production process of the present invention preferably, further, comprises a step (8) of preparing a crude hexafluoro-1,3-butadiene by dehydrating the crude hexafluoro-1,3-butadiene prepared in the step (7).

For the dehydration, a zeolite is preferably used. Examples thereof may include molecular sieves-3A, 4A and 5A. The dehydration process is preferably carried out at a temperature of from −15 to 60° C. It may be carried out in a gas phase or a liquid phase, preferably in a liquid phase. The dehydration process, further, is preferably carried out in at least two lines by a change over method.

Since the crude hexafluoro-1,3-butadiene prepared through the alkali contact step contains moisture, it is particularly preferred to successively dehydrate the crude hexafluoro-1,3-butadiene in a step (8) (dehydration process). The production process of the present invention preferably comprises the step (7) of allowing the mixture containing hexafluoro-1,3-butadiene prepared in the step (2) to contact with an alkali, thereby preparing the crude hexafluoro-1,3-butadiene, and the step (8) of dehydrating the resulting crude hexafluoro-1,3-butadiene prepared in the step (7), thereby preparing a crude hexafluoro-1,3-butadiene.

The production process of the present invention, further, comprises a step (9) of feeding the crude hexafluoro-1,3-butadiene prepared in the step (8) to at least two distillation columns and purifying it preferably. Specifically, the crude hexafluoro-1,3-butadiene is introduced into a first distillation column using a pump, a compressor or the like. In the first distillation column, low boiling components such as air, carbon monoxide, carbon dioxide and the like are extracted as a distillate extracted from the column top. As a distillate extracted from the column bottom, components essentially containing hexafluoro-1,3-butadiene are extracted and then introduced to a second distillation column.

In the second distillation column, a purified hexafluoro-1,3-butadiene, which is an objective distillate extracted from the column top, is recovered as a product. On the other hand, as a distillate extracted from the column bottom of the second distillation column, high boiling components such as a small amount of the solvent, the intermediate of the reaction in the step (2) and the like are extracted and at least one part of them can be circulated to the step (2).

Moreover, with regard to the another method, the crude hexafluoro-1,3-butadiene is firstly introduced into the first distillation column and low boiling components essentially containing the crude hexafluoro-1,3-butadiene are extracted as a distillate extracted from the column top. Further, small amounts of the high boiling components are extracted as a distillate extracted from the column bottom and these components can be circulated in the step (2).

Next, the low boiling components containing essentially hexafluoro-1,3-butadiene extracted from the column top are introduced to the second distillation column and the low boiling components such as air, carbon monoxide or carbon dioxide are extracted from the column top. From the column bottom, a purified hexafluoro-1,3-butadiene is extracted and recovered as a product.

As described above, in the step (2) according to the production process of the present invention, halogens except for a fluorine atom is eliminated by a metal from the 1,2,3,4-tetrachlorohexafluorobutane prepared in the step (1) in the reactor (B) and thereby the mixture containing hexafluoro-1,3-butadiene is prepared. In the step (2), it is preferred to feed at least one part of the high boiling components extracted from the bottom of the distillation column to the reactor (B).

That is to say, the present invention is summarized as follows.

The process for producing the hexafluoro-1,3-butadiene according to the present invention comprises (1) allowing 1,2,3,4-tetrachlorobutane to react with a fluorine gas in the presence of a diluting gas in a gas phase, thereby preparing 1,2,3,4-tetrachlorohexafluorobutane, and (2) dechlorinating the 1,2,3,4-tetrachlorohexafluorobutane prepared in the step (1) by a metal in the presence of the solvent, thereby preparing hexafluoro-1,3-butadiene.

In the step (1), the mixed gas (A) of 1,2,3,4-tetrachlorobutane and the diluting gas is fed to the reactor (A) having at least two feed openings from at least one feed opening and the mixed gas (B) of a fluorine gas and the diluting gas is fed from at least one of the other feed openings to allow the 1,2,3,4-tetrachlorobutane to react with a fluorine gas in the reactor (A) thereby preparing 1,2,3,4-tetrachlorohexafluorobutane. The concentration of 1,2,3,4-tetrachlorobutane is from 0.5 to 4 mol % based on the total amount of the mixed gases (A) and (B).

In the step (1), into the reactor (A) having at least two feed openings, the mixed gas (A) of 1,2,3,4-tetrachlorobutane and the diluting gas is fed through at least one feed opening and the mixed gas (B) of a fluorine gas and the diluting gas is fed through at least one of the other feed openings, to allow 1,2,3,4-tetrachlorobutane to react with a fluorine gas in the reactor (A), thereby preparing 1,2,3,4-tetrachlorohexafluorobutane. The concentration of the fluorine gas is from 0.5 to 10 mol % based on the total amount of the mixed gases (A) and (B).

In the step (1), 1,2,3,4-tetrachlorohexafluorobutane is preferably prepared by allowing 1,2,3,4-tetrachlorobutane to react with a fluorine gas at a pressure of from 0.05 to 1 MPa.

In the step (1), 1,2,3,4-tetrachlorohexafluorobutane is preferably prepared by allowing 1,2,3,4-tetrachlorobutane to react with a fluorine gas at a temperature of from 50 to 500° C.

In the step (2), hexafluoro-1,3-butadiene is preferably prepared by dechlorinating the 1,2,3,4-tetrachlorohexafluorobutane prepared in the step (1) with a metal.

The process for producing hexafluoro-1,3-butadiene according to the present invention comprises (1) a step of allowing 1,2,3,4-tetrachlorobutane to react with a fluorine gas in the presence of a diluting gas in a gas phase, thereby preparing a mixture containing 1,2,3,4-tetrachlorohexafluorobutane, and (2) a step of dechlorinating the 1,2,3,4-tetrachlorohexafluorobutane prepared in the step (1) with a metal in the presence of the solvent, thereby preparing a mixture containing hexafluoro-1,3-butadiene. The process, further, comprises (4) a step of liquid-liquid separating the mixture containing 1,2,3,4-tetrachlorohexafluorobutane prepared in the step (1) to prepare a 1,2,3,4-tetrachlorohexafluorobutane-rich phase, and allowing the resulting 1,2,3,4-tetrachlorohexafluorobutane-rich phase to contact with an alkali, thereby preparing crude 1,2,3,4-tetrachlorohexafluorobutane (A), and (5) a step of dehydrating the crude 1,2,3,4-tetrachlorohexafluorobutane (A) prepared in the step (4), thereby preparing crude 1,2,3,4-tetrachlorohexafluorobutane (B). The step (2) is characterized in that the crude 1,2,3,4-tetrachlorohexafluorobutane (B) prepared in the step (5) is dechlorinated by a metal to prepare a mixture containing hexafluoro-1,3-butadiene.

The mixture containing hexafluoro-1,3-butadiene contains the resulting hexafluoro-1,3-butadiene, unreacted 1,2,3,4-tetrachlorohexafluorobutane and the diluting gas. The crude 1,2,3,4-tetrachlorohexafluorobutane (A) prepared by removing hydrogen fluoride from the 1,2,3,4-tetrachlorohexafluorobutane-rich phase in the step (4) contains water and the intermediate of the reaction in the step (1). The crude 1,2,3,4-tetrachlorohexafluorobutane (B) from which water has been removed in the step (5) contains the intermediate of the reaction in the step (1).

Furthermore, the process preferably comprises the step (6) of feeding the crude 1,2,3,4-tetrachlorohexafluorobutane (B) prepared in the step (5) to at least one distillation column, separating the intermediate prepared in the step (1) and feeding at least one part of the intermediate to the reactor (A).

Moreover, the process preferably comprises the step (7) of allowing the mixture containing hexafluoro-1,3-butadiene prepared in the step (2) to contact with an alkali, thereby preparing the crude hexafluoro-1,3-butadiene (A), and the step (8) of dehydrating the crude hexafluoro-1,3-butadiene (A) prepared in the step (7), thereby preparing the crude hexafluoro-1,3-butadiene (B).

The crude hexafluoro-1,3-butadiene (A) prepared by removing hydrogen fluoride from the mixture containing hexafluoro-1,3-butadiene in the step (7) contains water and the intermediate of the reaction in the step (2). The crude hexafluoro-1,3-butadiene (B) prepared by removing water in the step (8) contains the intermediate of the reaction in the step (2).

Furthermore, the process preferably comprises the step (9) of purifying the crude hexafluoro-1,3-butadiene (B) prepared in the step (8) using at least two distillation columns.

In the step (2), the 1,2,3,4-tetrachlorohexafluorobutane prepared in the step (1) is dechlorinated by a metal in the reactor (B) to prepare the mixture containing hexafluoro-1,3-butadiene. It is preferred to feed at least one part of the high boiling components extracted from the column bottom of the distillation column to the reactor (B).

EXAMPLE

The present invention will be described with reference to the following examples. The present invention should not be limited with the examples.

Production Example 1,3-Butadiene produced industrially was chlorinated to prepare dichlorobutene. In the chlorination, a mixture of 3,4-dichlorobutene-1 and 1,4-dichlorobutene-2 was produced. The 1,4-dichlorobutene-2 is isomerized to 3,4-dichlorobutene-1. In the step of producing chloroprene from 3,4-dichlorobutene-1 by dehydrochlorination, other chlorine compounds were separated with distillation as a byproduct and then were made harmless and thrown away by burning treatment or the like.

The chlorine compounds produced as a byproduct were purified with separation by a distillation column to prepare 1,2,3,4-tetrachlorobutane. The other byproducts were made harmless by burning treatment. The resulting 1,2,3,4-tetrachlorobutane had a purity determined by gas chromatography analysis of 8.2 mol %.

Example 1

Step 1

A reactor made of Inconel 600 having an inner diameter of 20.6 mmø and a length of 600 mm equipped with two gas feed openings (heating method with an electric heater) was previously subjected to passivation treatment by a fluorine gas at a temperature of 550° C. To the reactor, a nitrogen gas was passed through in an amount of 25 NL/h (total 50 NL/h) from the two gas feed openings and the reactor was heated to 250° C. Furthermore, hydrogen fluoride was passed through in an amount of 15 NL/h, (total 30 NL/h) from each of the two gas feed openings. In this manner, a mixed gas of a nitrogen gas and hydrogen fluoride was used as a diluting gas.

Next, one of the diluting gas flow branched in an amount of 40 NL/h and the 1,2,3,4-tetrachlorobutane prepared in the production example in an amount of 1.0 NL/h were simultaneously fed to the reactor. Thereafter, the other diluting gas flow branched in an amount of 40 NL/h and a fluorine gas in an amount of 6.1 NL/h were simultaneously fed to the reactor and then the reaction was started.

The reaction results in the step (1) were evaluated in the following manner. After 3 hours from the reaction start, a reaction generated gas obtained from an outlet of the reactor (a mixture containing 1,2,3,4-tetrachlorohexafluorobutane prepared in the step (1)) was treated with potassium hydroxide and an aqueous solution of potassium iodide to remove hydrogen fluoride, unreacted fluorine gas and nitrogen gas which were contained in the reaction generated gas. Next, the mixture was extracted with an organic solvent and the composition of an extracting liquid was determined by gas chromatography. The results are shown below

| | |
|---|---|
| 1,2,3,4-tetrachlorohexafluorobutane | 92.2% |
| Other components | 7.8% |

(unit: vol %)

After about 5 hours from the reaction start, a reaction gas obtained from the outlet (a mixture containing 1,2,3,4-tetrachlorohexafluorobutane prepared in the step (1)) was collected with cooling and cooled to separate into a hydrogen fluoride-rich phase and a 1,2,3,4-tetrachlorohexafluorobutane-rich phase. In this separation, a nitrogen gas was also removed. The 1,2,3,4-tetrachlorohexafluorobutane-rich phase was extracted and washed with an alkali. Thereafter, the phase was subjected to dehydration treatment by molecular sieves to prepare crude 1,2,3,4-tetrachlorohexafluorobutane. Next, the crude 1,2,3,4-tetrachlorohexafluorobutane was purified with distillation to prepare a 1,2,3,4-tetrachlorohexafluorobutane purified product. The product was analyzed by gas chromatography. As a result, the product had a purity of 99.0 mol %.

Step 2

To a 500 mL internal volume autoclave made of SUS316 (jacket heating method) equipped with a jacket having a cooling structure on the upper part, and a stirrer, 119 g of isopropyl alcohol as a solvent, 149 g of the 1,2,3,4-tetrachlorohexafluorobutane prepared in the step (1) and 20 g of a granular metal zinc were fed.

While the mixture was stirred, the temperature was elevated to 70° C., and then 62.4 g of a granular metal zinc was further added while keeping the temperature. In this addition, the metal zinc was dividedly added by three times, namely the metal zinc was added in a total amount of 82.4 g. Thereafter, the reaction was carried out for 16 hr.

After the 16 hr reaction, the reactant was heated and then the solvent and organic products were collected with cooling and the solvent was removed by known separation with distillation. The resulting product was analyzed by gas chromatography. The results are as follows.

| Hexafluoro-1,3-butadiene | 94.5% |
|---|---|
| Other components | 5.5% |

(unit: vol %)

The product was subjected to dehydrating treatment by molecular sieves, and then subjected to extraction of a high boiling cut and extraction of a low boiling cut using two distillation columns to prepare hexafluoro-1,3-butadiene (purified product 1). The purified product was analyzed by gas chromatography. As a result, in the purified product 1, hexafluoro-1,3-butadiene had a purity of more than 99.995 vol %. Moreover, the purified product was further subjected to extraction of a low boiling cut using the other distillation column to prepare hexafluoro-1,3-butadiene (purified product 2). In the purified product 2, the hexafluoro-1,3-butadiene had a purity of more than 99.999%.

The invention claimed is:

1. A process for producing hexafluoro-1,3-butadiene comprising:
   (1) a step comprising allowing a compound having four carbon atoms each which bonds to an atom selected from the group consisting of a bromine atom, an iodine atom and a chlorine atom, to react with a fluorine gas in the presence of a diluting gas in a gas phase, thereby preparing a mixture containing a product (A), and
   (2) a step comprising eliminating halogens excluding a fluorine atom with a metal from the product (A) prepared in the step (1) in the presence of a solvent, thereby preparing a mixture containing hexafluoro-1,3-butadiene.

2. The process for producing hexafluoro-1,3-butadiene according to claim 1 wherein the step (1) comprises allowing a compound having four carbon atoms to react with a fluorine gas in the absence of a catalyst, thereby preparing a mixture containing the product (A).

3. The process for producing hexafluoro-1,3-butadiene according to claim 1 which process further comprises a step (3) of halogenating 1,3-butadiene, thereby preparing the compound having four carbon atoms wherein the step (1) comprises allowing the compound having four carbon atoms prepared in the step (3) to react with a fluorine gas, thereby preparing a mixture containing the product (A).

4. The process for producing hexafluoro-1,3-butadiene according to claim 1 wherein the diluting gas is at least one gas selected from the group consisting of nitrogen, helium, argon, neon and hydrogen fluoride.

5. The process for producing hexafluoro-1,3-butadiene according to claim 1 wherein the step (1) comprises allowing 1,2,3,4-tetrachlorobutane to react with a fluorine gas in the presence of a diluting gas in a gas phase, thereby preparing a mixture containing 1,2,3,4-tetrachlorohexafluorobutane, and the step (2) comprises dechlorinating the 1,2,3,4-tetrachlorohexafluorobutane prepared in the step (1) with a metal in the presence of a solvent, thereby preparing a mixture containing hexafluoro-1,3-butadiene.

6. The process for producing hexafluoro-1,3-butadiene according to claim 5 wherein the step (1) comprises allowing 1,2,3,4-tetrachlorobutane to react with a fluorine gas in a reactor (A) having at least two feed openings by feeding a mixed gas (A) of 1,2,3,4-tetrachlorobutane and the diluting gas from at least one feed opening and feeding a mixed gas (B) of a fluorine gas and the diluting gas from at least one of the other openings, thereby preparing a mixture containing 1,2,3,4-tetrachlorohexafluorobutane, and the concentration of 1,2,3,4-tetrachlorobutane is from 0.5 to 4% by mole based on the total amount of the mixed gases (A) and (B).

7. The process for producing hexafluoro-1,3-butadiene according to claim 5 wherein the step (1) comprises allowing 1,2,3,4-tetrachlorobutane to react with a fluorine gas in a reactor (A) having at least two feed openings by feeding a mixed gas (A) of 1,2,3,4-tetrachlorobutane and the diluting gas from at least one feed opening and feeding a mixed gas (B) of a fluorine gas and the diluting gas from at least one of the other openings, thereby preparing a mixture containing 1,2,3,4-tetrachlorohexafluorobutane, and the concentration of a fluorine gas is from 0.5 to 10% by mole based on the total amount of the mixed gases (A) and (B).

8. The process for producing hexafluoro-1,3-butadiene according to claim 5 wherein the step (1) comprises allowing 1,2,3,4-tetrachlorobutane to react with a fluorine gas at a pressure of from 0.05 to 1 MPa, thereby preparing a mixture containing 1,2,3,4-tetrachlorohexafluorobutane.

9. The process for producing hexafluoro-1,3-butadiene according to claim 5 wherein the step (1) comprises allowing 1,2,3,4-tetrachlorobutane to react with a fluorine gas at a temperature of from 50 to 500° C., thereby preparing a mixture containing 1,2,3,4-tetrachlorohexafluorobutane.

10. The process for producing hexafluoro-1,3-butadiene according to claim 1 or 5 wherein the solvent is an organic solvent and/or water.

11. The process for producing hexafluoro-1,3-butadiene according to claim 10 wherein the organic solvent is an alcohol.

12. The process for producing hexafluoro-1,3-butadiene according to claim 11 wherein the alcohol is at least one selected from the group consisting of methanol, ethanol, isopropyl alcohol and octanol.

13. The process for producing hexafluoro-1,3-butadiene according to claim 1 or 5 wherein the metal is at least one selected from the group consisting of Mg, Zn, Al, Cu, Na and Li.

14. The process for producing hexafluoro-1,3-butadiene according to claim 5 wherein the step (2) comprises dechlorinating the 1,2,3,4-tetrachlorohexafluorobutane prepared in the step (1), with a metal at a temperature of from 20 to 150° C., thereby preparing a mixture containing hexafluoro-1,3-butadiene.

15. The process for producing hexafluoro-1,3-butadiene according to claim 5 which further comprises:
- a step (4) of liquid-liquid separating the mixture containing 1,2,3,4-tetrachlorohexafluorobutane prepared in the step (1) and allowing a resulting 1,2,3,4-tetrachlorohexafluorobutane-rich phase to contact with an alkali, thereby preparing crude 1,2,3,4-tetrachlorohexafluorobutane, and
- a step (5) of dehydrating the crude 1,2,3,4-tetrachlorohexafluorobutane prepared in the step (4), thereby preparing crude 1,2,3,4-tetrachlorohexafluorobutane, wherein the step (2) comprises dechlorinating the crude 1,2,3,4-tetrachlorohexafluorobutane prepared in the step (5), with a metal, thereby preparing a mixture containing hexafluoro-1,3-butadiene.

16. The process for producing hexafluoro-1,3-butadiene according to claim 15 which further comprises a step (6) of feeding the crude 1,2,3,4-tetrachlorohexafluorobutane prepared in the step (5), to a distillation column, separating an intermediate in the step (1) and feeding at least a part of the intermediate to the reactor (A).

17. The process for producing hexafluoro-1,3-butadiene according to claim 5 which further comprises:
- a step (7) of allowing the mixture containing the hexafluoro-1,3-butadiene prepared in step (2) to contact with an alkali, thereby preparing crude hexafluoro-1,3-butadiene, and
- a step (8) of dehydrating the crude hexafluoro-1,3-butadiene prepared in the step (7), thereby preparing crude hexafluoro-1,3-butadiene.

18. The process for producing hexafluoro-1,3-butadiene according to claim 17 which further comprises a step (9) of purifying the crude hexafluoro-1,3-butadiene prepared in the step (8) by means of at least two distillation columns.

19. The process for producing hexafluoro-1,3-butadiene according to claim 18 wherein the step (2) comprises dechlorinating the 1,2,3,4-tetrachlorohexafluorobutane prepared in the step (1) with a metal in a reactor (B), thereby preparing a mixture containing hexafluoro-1,3-butadiene, and at least a part of a high boiling component taken out from a column bottom of the distillation column is fed to the reactor (B).

* * * * *